United States Patent [19]

Takeuchi et al.

[11] Patent Number: 5,117,052
[45] Date of Patent: May 26, 1992

[54] PHYSIOLOGICALLY ACTIVE SUBSTANCES, BENASTATINS A AND B, AND PRODUCTION AND USE THEREOF

[75] Inventors: Tomio Takeuchi, Tokyo; Takaaki Aoyagi, Fujisawa; Hiroshi Naganawa, Tokyo; Masa Hamada, Tokyo; Yasuhiko Muraoka, Tokyo; Takayuki Aoyama, Tokyo, all of Japan

[73] Assignee: Zaidan Hojin Biseibutsu Kagaku Kenkyu Kai, Tokyo, Japan

[21] Appl. No.: 669,387

[22] Filed: Mar. 14, 1991

[30] Foreign Application Priority Data

Mar. 16, 1990 [JP] Japan .................. 2-066723
Aug. 3, 1990 [JP] Japan .................. 2-206130

[51] Int. Cl.$^5$ .................. C07C 59/76; A01N 37/10
[52] U.S. Cl. .................. 562/461
[58] Field of Search .................. 562/461

[56] References Cited

PUBLICATIONS

Hollingworth, R. et al., Life Sci 13(3) 191-199, 1973.
Past, M. et al., Biochem. Biophys. Res Commun 52(4) 1123-8, 1973.
Ohkawa, H. et al., Pestic. Biochem. Physiol. 2(1) 95-112, 1972.
Ohkawa, H. et al. Biochem Pharmacol. 1973, 20(7) 1708-1711.

Primary Examiner—Paul J. Killos
Attorney, Agent, or Firm—Nields & Lemack

[57] ABSTRACT

Benastatins A and B which are novel and physiologically active substances having the formula

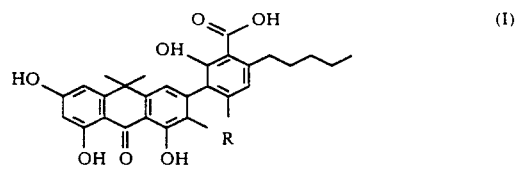

wherein R represents —CH$_2$—CH$_2$— or —CH=CH—, exhibit a potent immunomodifier activity, a glutathione transferase inhibition activity and an antimicroorganism activity and are therefore extremely useful for various drugs.

3 Claims, 8 Drawing Sheets

PHYSIOLOGICALLY ACTIVE SUBSTANCES, BENASTATINS A AND B, AND PRODUCTION AND USE THEREOF

BACKGROUND OF THE INVENTION

1. Field of the Invention

The present invention relates to benastatins A and B, which are novel, physiologically active substances having an anti-glutathione transferase activity, an immunomodifier activity and a microorganism-controlling actvity, and also to the production and the use thereof.

2. Related Art Statement

Glutathione transferase is an enzyme locally present in cell membranes and cytoplasms.

It is known that cell membrane enzyme inhibitors have an immunomodifier activity [T. Aoyagi, "Protease inhibitor and biological control", Bioactive Metabolites from Microorganisms, ed. by M. E. Bushell and U. Gäfe, pp. 403-418, Elsevier Science Publishers B.V., Amsterdam, (1989)]. It may therefore be expected that a glutathione transferase inhibitor would also have an immunomodifier activity.

It is also known that membrane-connecting glutathione transferases have an activity as leukotriene $C_4$ synthesis enzymes, and have a close relation with inflammations and allergic reactions [Tanpakushitsu, Kakusan, Kouso (Proteins, Nucleic Acids and Enzymes), 33, 1564-1573 (1988)].

Furthermore, it is reported that cytoplasmic glutathione transferases have a close relation with the resistance mechanism of anticancer agent-resistant tumor cells [Gan-to Kagaku Ryoho (Cancers and Chemotherapies), 16, 592-598 (1989)].

Known glutathione transferase inhibitors include indomethacin, meclofenamic acid and the like [Biochemical and Biophysical Research Communications, 112, 980-985 (1983)].

Known glutathione transferase inhibitors such as indomethacin and meclofenamic acid, etc., have a low specificity to glutathione transferases. It is therefore desired to provide an inhibitor substance highly specific to glutathione transferases.

SUMMARY OF THE INVENTION

It is an object of the invention to provide physiologically active substances having a highly specific glutathione transferase inhibition activity and further having an immunomodifier activity and a microorganism-controlling activity, and to provide a process for the preparation of the substances, and the use of the substances.

Therefore, in the first aspect of the present invention, there are provided benastatins A and B, which are novel, physiologically active substances having the formula (I):

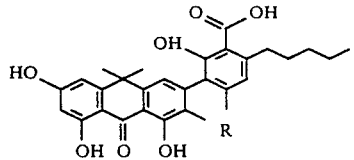

(I)

wherein R represents —CH$_2$—CH$_2$— or —CH=CH—, and phamaceutically acceptable salts thereof.

In the second aspect of the invention, there is provided a process for the preparation of benastatin A or B, which comprises the steps of:
culturing benastatin-producing bacteria belonging to Streptomyces; and
separating benastatin A or B thus produced from the culture medium.

In the third aspect of the invention, there is provided a pharmaceutical composition for the inhibition of glutathione transferase, for immunomodification or for the control of microorganism, which comprises benastatin A or B or a pharmaceutically acceptable salt thereof as an active ingredient and a pharmaceutically acceptable carrier.

In the fourth aspect of the invention, there is provided a method for the inhibition of glutathione transferase, for immunomodification or for the control of microorganism, which comprises administering an effective amount of benastatin A or B or a pharmaceutically acceptable salt thereof to a warm-blooded animal.

In the fifth aspect of the invention, there is provided a method for immunomosuppression, which comprises administering an effective amount of benastatin A or a pharmaceutically acceptable salt thereof to a warm-blooded animal.

In the sixth aspect of the invention, there is provided a method for immunomopotentiation, which comprises administering an effective amount of benastatin B or a pharmaceutically acceptable salt thereof to a warm-blooded animal.

DETAILED EXPLANATION OF THE DRAWINGS

DETAILED DESCRIPTION OF THE INVENTION

Of the compounds having the formula (I), benastatin A wherein R represents —CH=CH— has the formula:

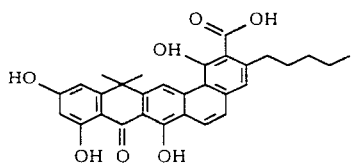

Figure 1:
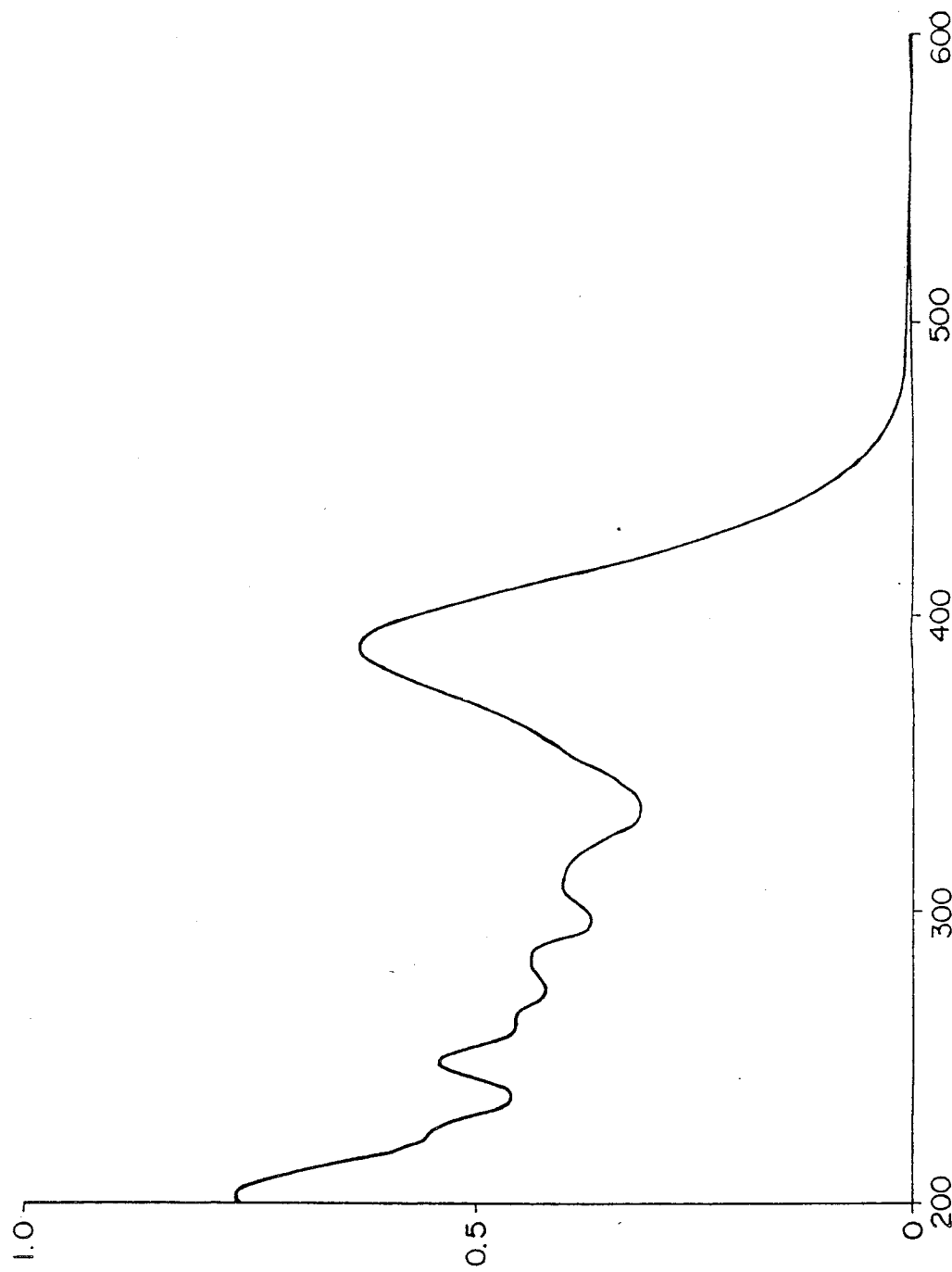
FIG. 1 shows an ultraviolet absorption spectrographic chart of a solution of 10 μg/ml of benastatin A in ethanol.
Figure 2:
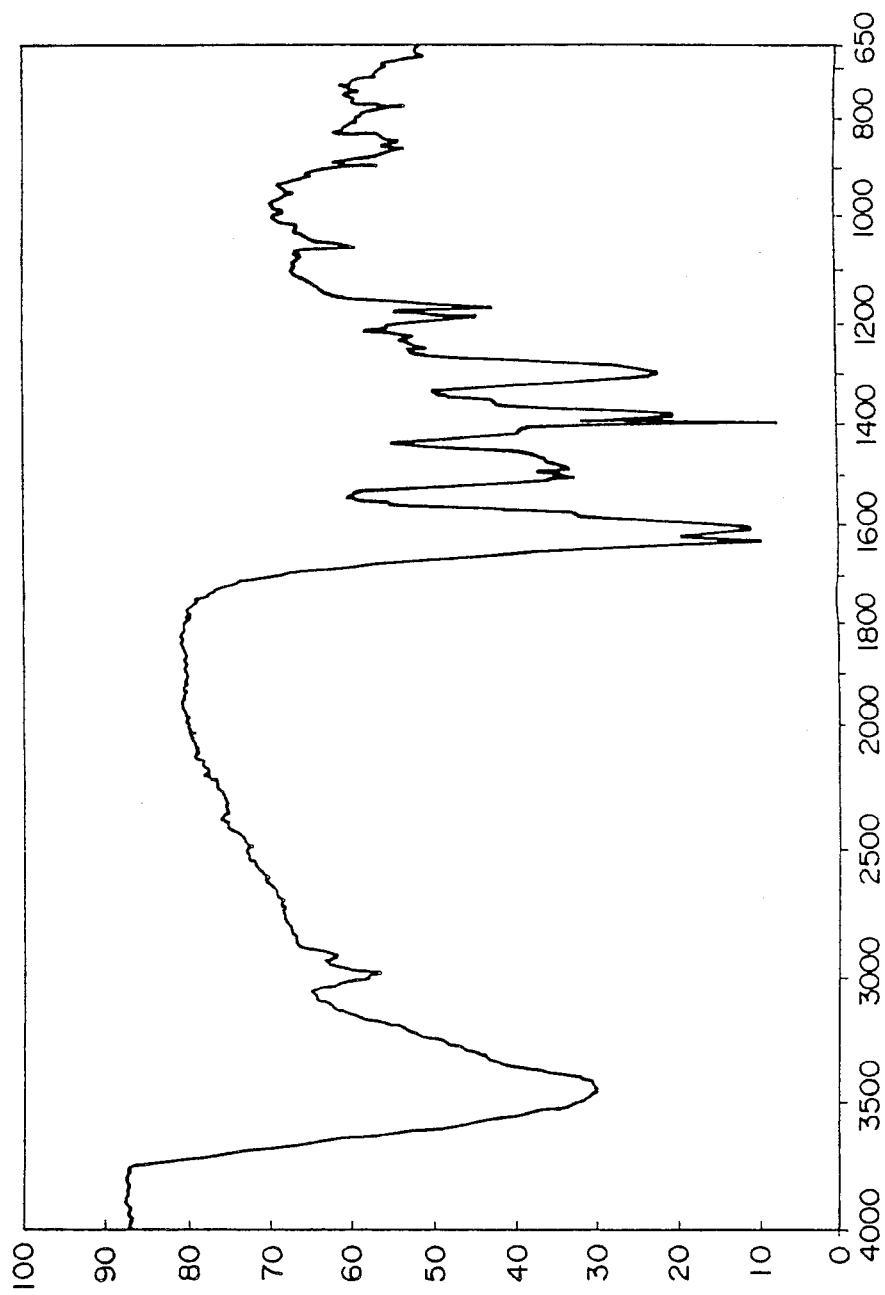
FIG. 2 shows an infrared absorption spectrographic chart of benastatin A contained in a potassium bromide tablet.
Figure 3:
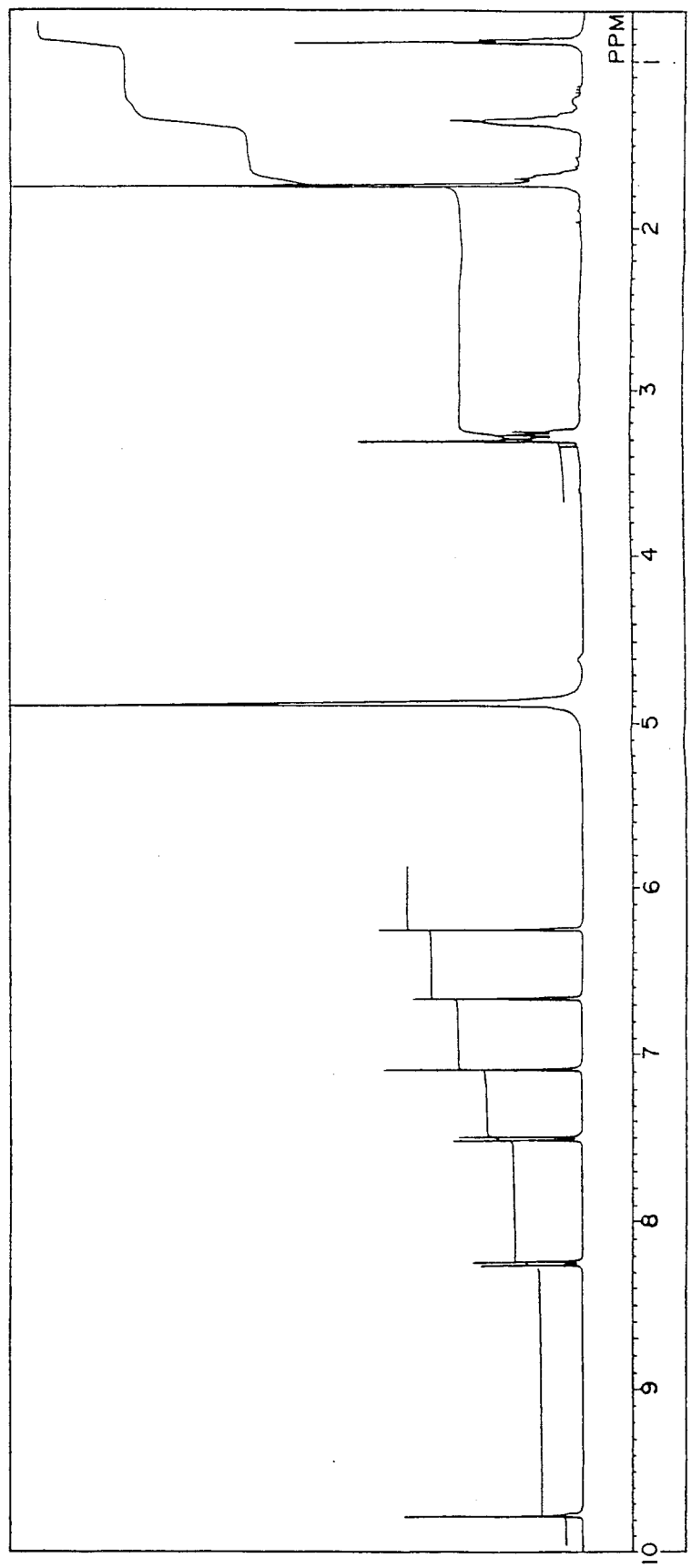
FIG. 3 shows an $^1$H-NMR spectrographic chart (400 MHz) of benastatin A measured in deuterium-containing methanol.
Figure 4:
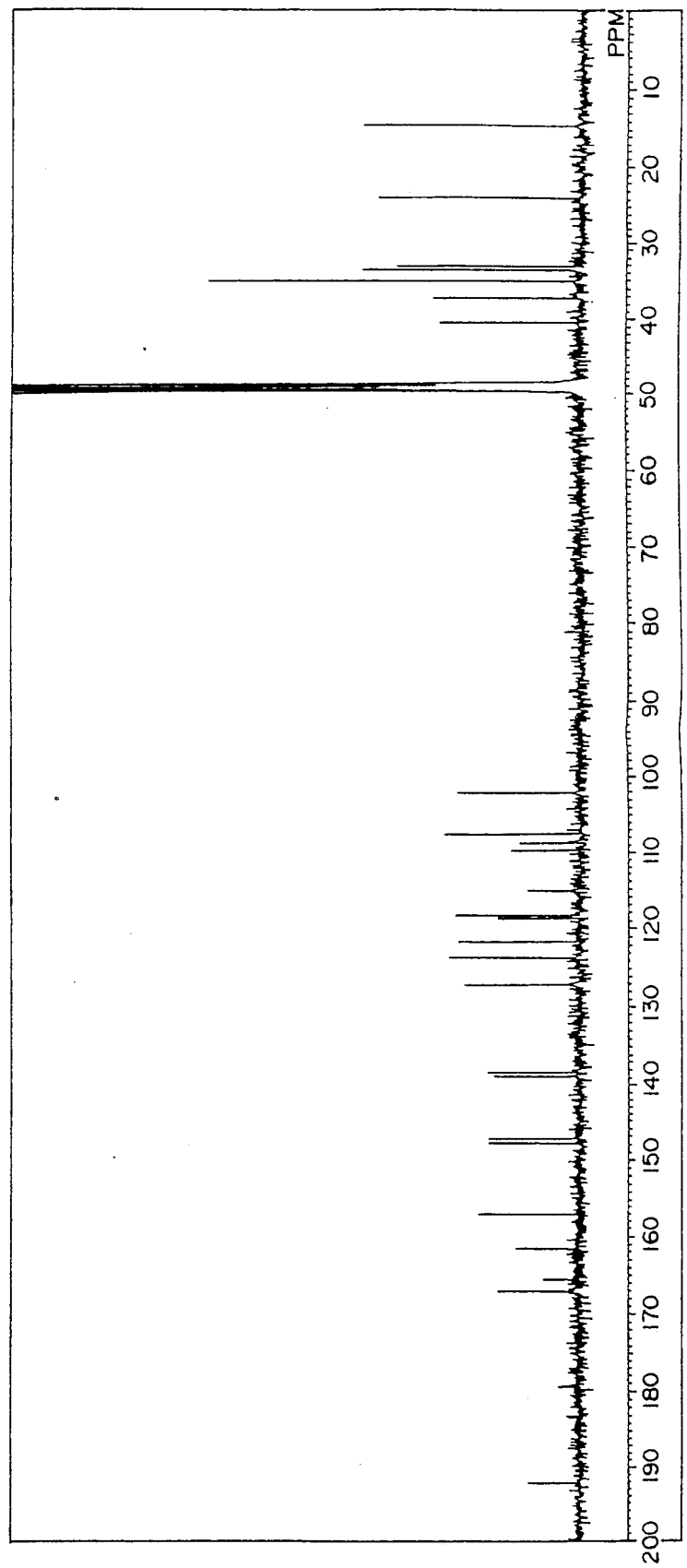
FIG. 4 shows a $^{13}$C-NMR spectrographic chart (100 MHz) of benastatin A measured in deuterium-containing methanol.

The physical and chemical properties of benastatin A are as follows.
(1) Color and shape: Yellow powder
(2) Molecular formula: $C_{30}H_{28}O_7$
(3) Molecular weight: 500 (FAB-MS (negative) m/z 499 $(M-H)^-$)
(4) Melting point: 170°–173° C. (dec.)
(5) UV-absorption spectra: FIG. 1.
(6) IR-absorption spectra: FIG. 2.
(7) $^1$H-NMR spectra: FIG. 3.
(8) $^{13}$C-NMR spectra: FIG. 4.
(9) Solubility: soluble in dimethyl sulfoxide, methanol, acetone and ethyl acetate, and insoluble in water.
(10) Thin layer chromatography (silica gel "Art. 5715" (Merck Company); eluant: chloroform-methanol (4:1): Rf=0.37.

Of the compounds having the formula (I), benastatin B wherein R represents $-CH_2CH_2-$ has the formula:

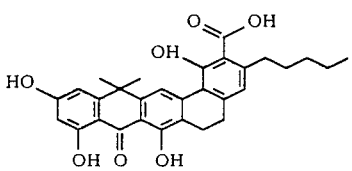

Figure 5:
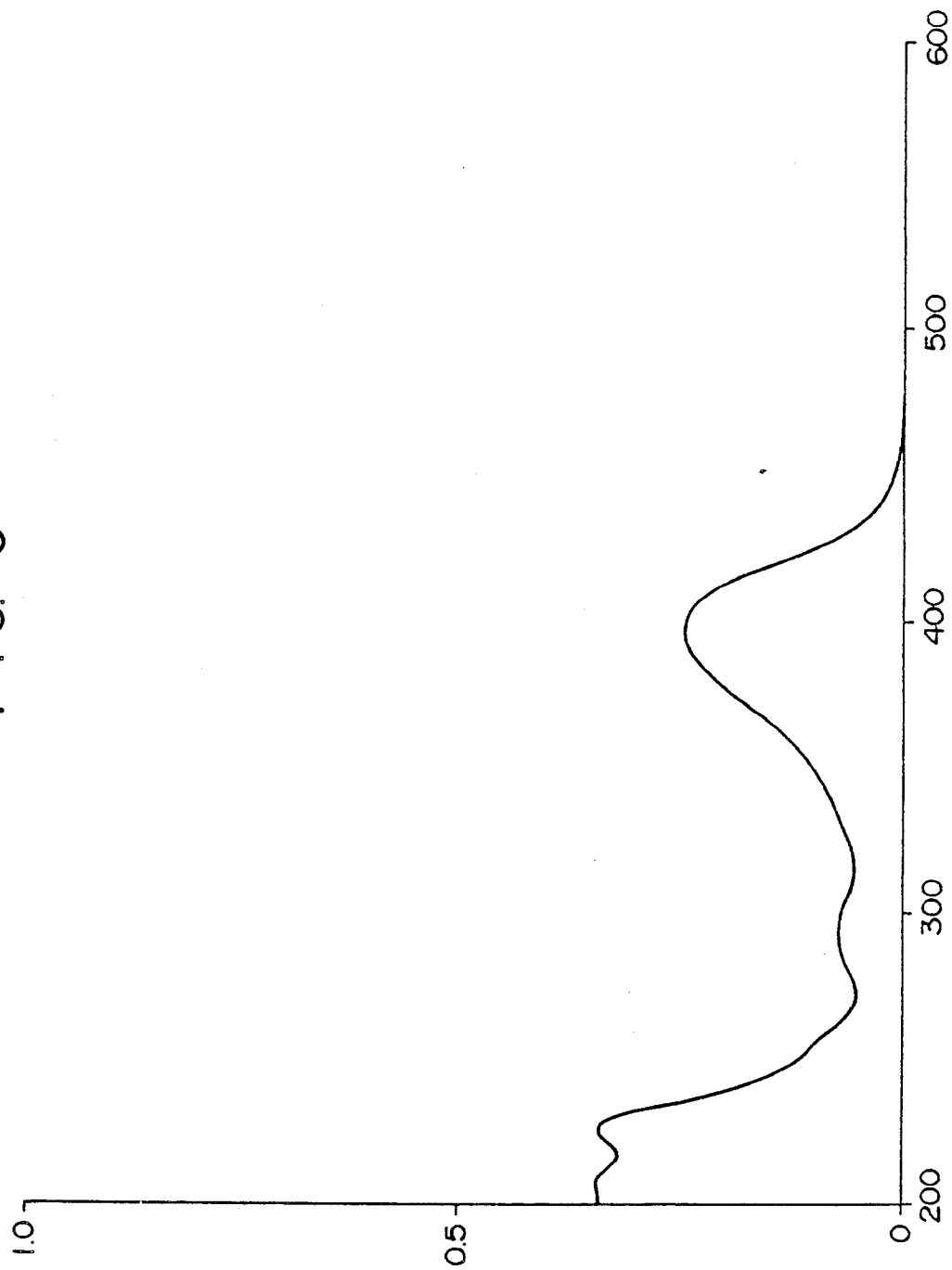
FIG. 5 shows an ultraviolet absorption spectrographic chart of a solution of 10 μg/ml of benastatin B in ethanol.
Figure 6:
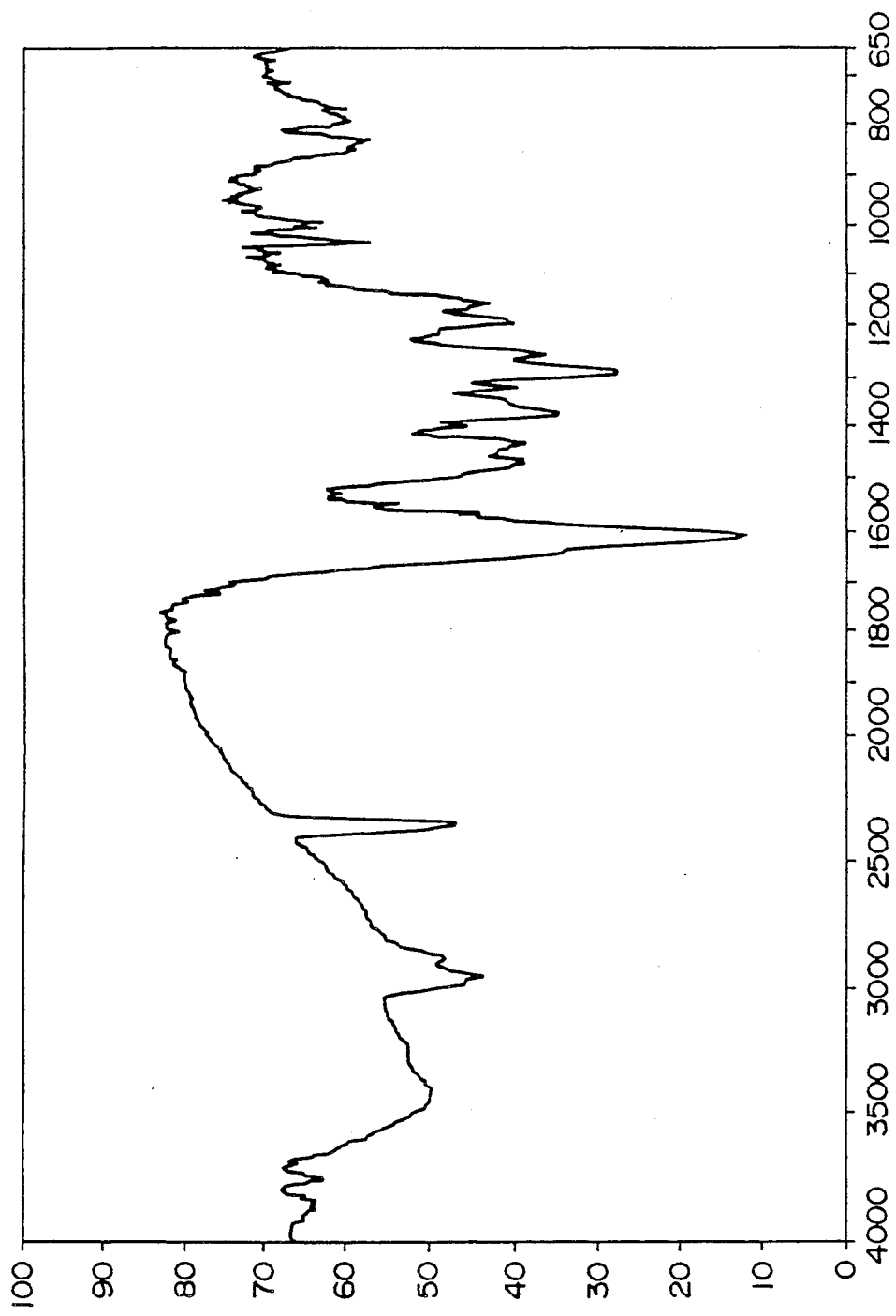
FIG. 6 shows an infrared absorption spectrographic chart of benastatin B contained in a potassium bromide tablet.
Figure 7:
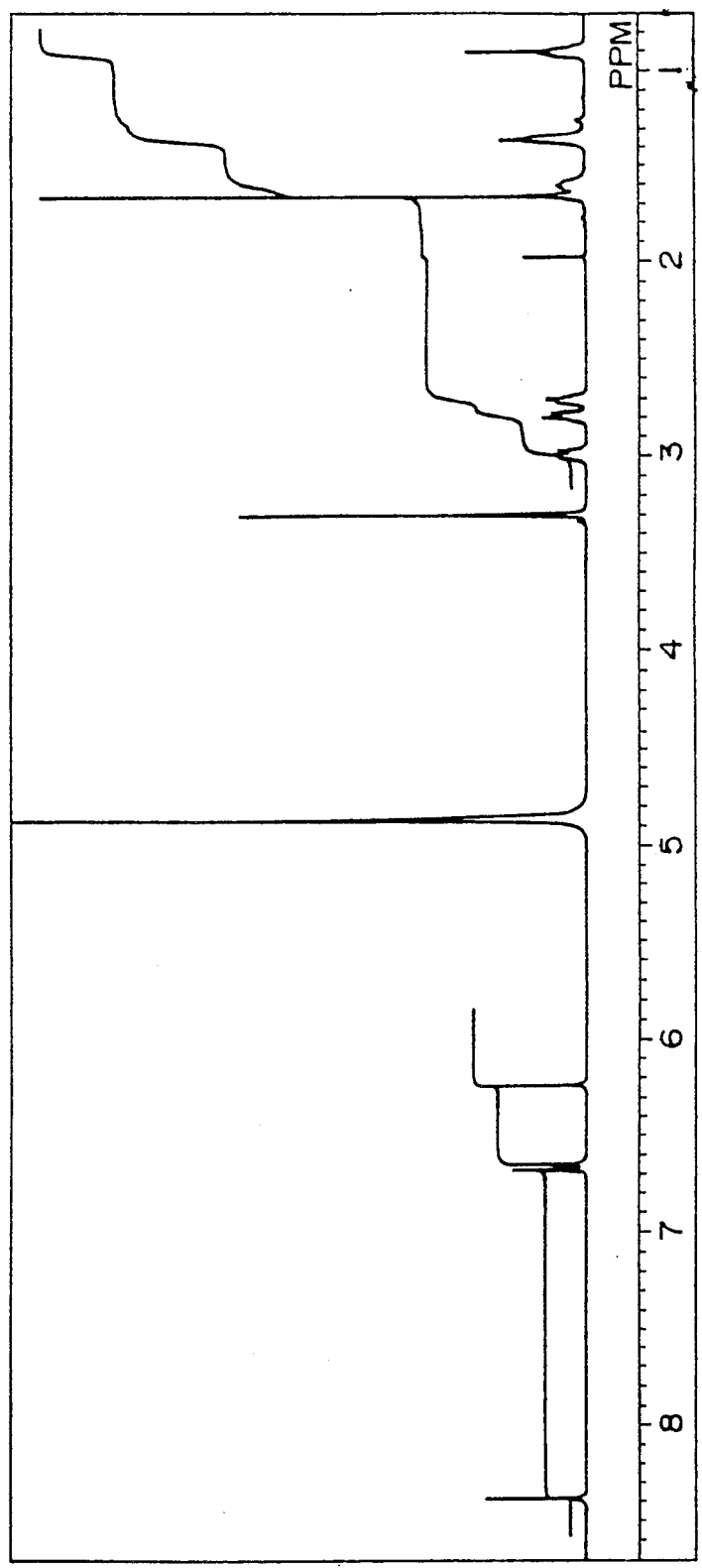
FIG. 7 shows an $^1$H-NMR spectrographic chart (400 MHz) of benastatin B measured in deuterium-containing methanol.
Figure 8:
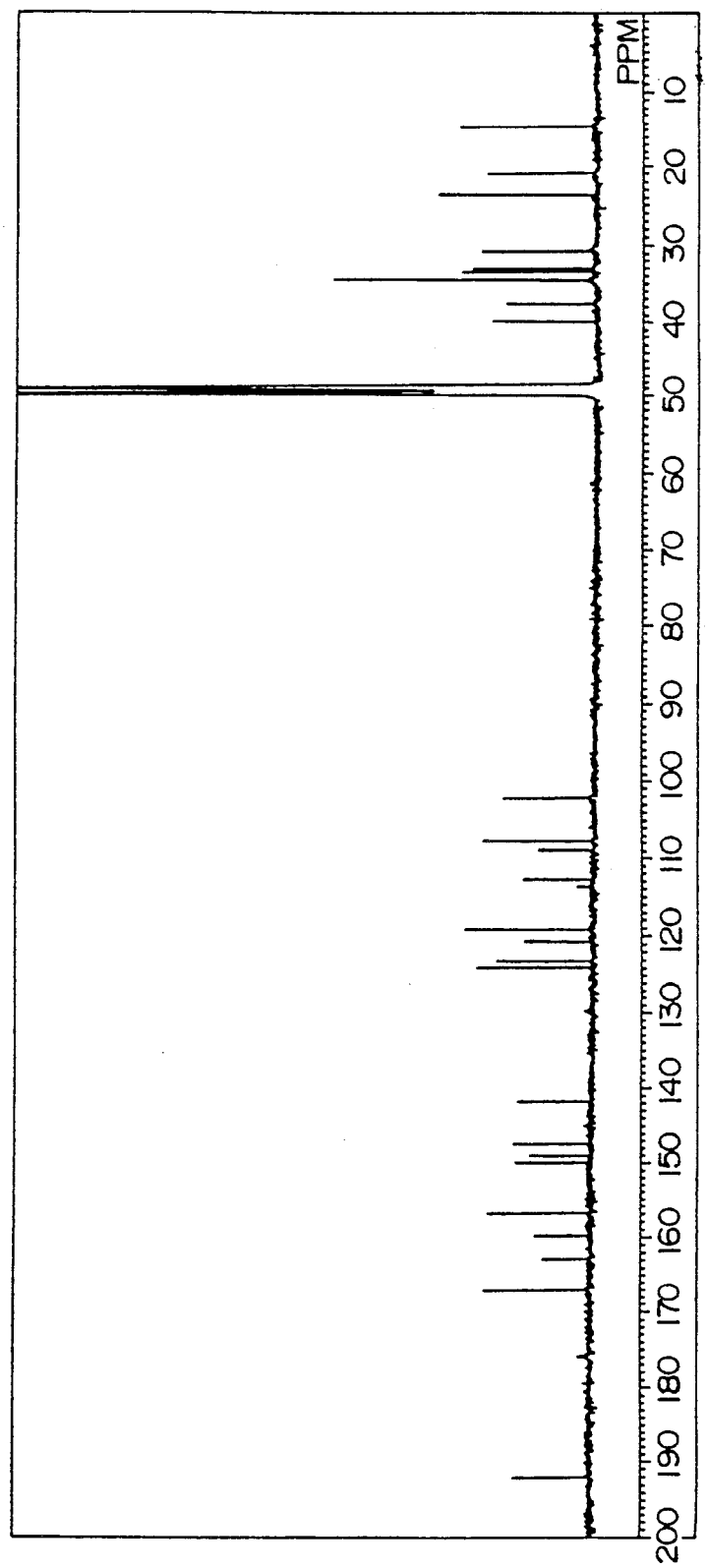
FIG. 8 shows a $^{13}$C-NMR spectrographic chart (100 MHz) of benastatin B measurd in deuterium-containing methanol.

The physical and chemical properties of benastatin B are as follows.
(1) Color and shape: Yellow powder
(2) Molecular formula $C_{30}H_{30}O_7$ (3) Molecular weight: 502 (FAB-MS (negative) m/z 501 $(M-H)^-$)
(4) Melting point: 210°–212° C. (dec.)
(5) UV-absorption spectra: FIG. 5.
(6) IR-absorption spectra: FIG. 6.
(7) $^1$H-NMR spectra: FIG. 7.
(8) $^{13}$C-NMR spectra: FIG. 8.
(9) Solubility: soluble in dimethyl sulfoxide, methanol, acetone and ethyl acetate, and insoluble in water.
(10) Thin layer chromatography (silica gel "Art. 5715"(Merck Company); eluant: chloroform-methanol (4:1): Rf=0.44.

Benastatin A and B may also be present in the form of pharmaceutically acceptable salts. Examples of such salts includes, for instance, salts of alkali metals such as sodium, potassium, lithium and the like, and salts of alkaline earth metals such as calcium and the like.

In the second aspect of the invention, there is provided a process for the preparation of benastatin A or B, which comprises the steps of:
culturing benastatin-producing bacteria belonging to Streptomyces; and
separating benastatin A or B thus formed from the culture medium.

As an example of the benastatin-producing microorganisms, there may be mentioned a Streptomyces strain MI384-DF12, which has been found by the present inventors in a soil in Suginami-Ku, Tokyo, Japan. The microbiological properties of strain MI384-DF12 are as follows.

1. Shape

Under the microscope, it is observed that microorganisms of strain MI384-DF12 have branched primary hyphae, and aerial hyphae extended from the primary hyphae. The aerial hyphae usually extend straightforwards and have spiral spore chains with at least 20 spores. It is a characteristic feature of the microorganisms that they have a pseudosporangium with a diameter of 1.5 to 6 microns. No verticillate branches as well as no sporangia have been observed. The spores have a size of $0.5-0.6 \times 0.7-0.8$ microns, and the spore surface is smooth.

2. Growth in culture media

For the identification of colors, use was made of "Color Harmony Manual", Container Corporation of America.

(1) Sucrose-nitrate salt-agar culture medium (cultivation at 27° C.)

The microorganisms have a color of light brown (4 ng, Lt Brown) to dark brown (3 pn, Dk Brown). No adherence of aerial hyphae has been observed. There are soluble pigments having a faint brown shade.

(2) Glucose-asparagine-agar culture medium (cultivation at 27° C.)

The microorganisms have a color of light brown (3 ie, Camel) to reddish brown (5 ui, Rosewood Brown). No adherence of aerial hyphae has been observed. There are soluble pigments having a faint pink shade.

(3) Glycerine-aspargine-agar culture medium (ISP-culture medium 5, cultivation at 27° C.)

The microorganisms have a color of brownish (gray 94 ni, Spice Brown) to dark olive gray (1 po, Ebony), and have white aerial hyphae sparsely grown thereon. There are soluble pigments having a faint pink color. When a 0.05N NaOH is added, the microorganisms and the soluble pigments make a color change so as to have a greenishshade. On the other hand, when a 0.05N HCl is added, there is no color change. (4) Starch-inorganic salt-agar culture medium (ISP-culture medium 4, cultivation at 27° C.)

There have been observed microorganisms having a color of brownish gray (4 ni, Spice Brown) to dark brown (4 pn, Dk Brown), and having cotton-like white aerial hyphae grown thereon. There are soluble pigments having a faint brown color. When a 0.05N NaOH is added, the microorganisms and the soluble pigments make a color change so as to have a greenishshade. When a 0.05N HCl is added, no color change is made.

(5) Tyrosine-agar culture medium (ISP-culture medium 7, cultivation at 27° C.)

The microorganisms have a color of grayish brown (3 ni, Clove Brown) to dark brown (4 nl, Dk Brown). No adherence of aerial hyphae has been observed. There are soluble pigments having a brownish shade.

(6) Nutritive agar culture medium (cultivation at 27° C.)

The microorganisms have a color of light brown (3 ng, Yellow Maple) to grayish brown (3 ni, Clove Brown). No adherence of aerial hyphae has been observed. There are soluble pigments having a brown shade.

(7) Yeast-malt-agar culture medium (ISP-culture medium 2, cultivation at 27° C.)

There are observed microorganisms having a color of light yellow brown (2 pg, Mustard Gold) to light brown (2 ni, Mustard Brown), and having cotton-like white aerial hyphae grown thereon. There are no soluble pigments.

(8) Oatmeal-agar culture medium (ISP-culture medium 3, cultivation at 27° C.)

The microorganisms have a color of light pink (5 ba, Shell Pink) to light yellow brown(2 lg, Mustard Tan), and having aerial hyphae with a light gray color (13 cb, Pearl Gray) sparsely grown thereon. There are soluble pigments having a light pink shade.

(9) Glycerine-nitrate salt-agar culture medium (cultivation at 27° C.):

The microorganisms have a color of light pink (6 lg, Dk Redwood) No adherence of aerial hyphae has been observed. There are soluble pigments having a faint pink shade.

(10) Starch-agar culture medium (cultivation at 27° C.)

The microorganisms have a color of light brown (3 ng, Yellow Maple) to dark brown (4 pn, Dk Brown). No adherence of aerial hyphae has been observed. There soluble pigments having a faint pink shade.

(11) Calcium malate-agar culture medium (cultivation at 27° C.)

The microorganisms have a color of light olive color (1 le, Olive Yellow). No adherence of aerial hyphae has been observed. There are no soluble pigments.

(12) Cellulose culture medium (Filter paper-added synthetic solution, cultivation at 27° C.)

No growth of microporganisms was observed when the cultivation was effected for 3 weeks.

(13) Gelatin cultivation (simple gelatin culture medium, 15% gelatin, cultivation at 20° C.; and glucose-peptone-gelatin culture medium, cultivation at 24° C.)

In the case of simple gelatin culture medium, the microorganisms have a light brown color. No adherence of aerial hyphae has been observed. There are soluble pigments having a brown shade.

In the case of glucose-peptone-gelatin culture medium, the microorganisms have a light yellow color No adherence of aerial hyphae has been observed. There are soluble pigments having a brown shade.

(14) Skimmed milk culture medium (cultivation at 37° C.)

The microorganisms have a light brown color. No adherence of aerial hyphae has been observed. There are soluble pigments having a brown shade.

3. PHYSIOLOGICAL PROPERTIES (1) Growth temperatures

A test was made in the following manner. A cultivation was conducted in a yeast-starch-agar culture medium (1.0% soluble starch, 0.2% yeast extract and 3.0% agar: pH 7.0) at a temperature of 20° C., 24° C., 27° C., 30° C. or 50° C. It was observed that the microorganisms had grown at a temperature of 20° C., 24° C., 27° C., 30° C. or 37° C. At 20° C., a poor growth was observed. At 50° C, no growth was observed. It is therefore considered that a temperature of about 27° to 30° C. is the optimum growth temperature.

(2) Liquefaction of gelatin culture medium (15% simple gelatin culture medium, cultivation at 20° C.; or glucose-peptone-gelatin culture medium, cultivation at 27° C.)

In the case of 15% simple gelatin culture medium, no liquefaction was observed. In the case of glucose-peptone-gelatin culture medium, a weak liquefaction was observed after 21 days from the start of the cultivation. The liquefaction intensity is rather low.

(3) Hydrolysis of starch (starch-inorganic salt-agar culture medium, or starch-agar culture medium, cultivation at 27° C. in either case)

In both the starch-inorganic salt-agar culture medium and the starch-agar culture medium, a hydrolysis was observed after about 3 days from the start of the cultivation. The hydrolysis was of a middle strength.

(4) Coagulation and peptonation of skimmed milk (skimmed milk, cultivation at 37° C.)

A peptonation started after about 6 days, and ceased after about 13 days from the beginning of the cultivation. This peptonation was of a middle or relatively high strength. No coagulation was observed.

(5) Formation of melanine-like pigments (tryptone-yeast-broth culture medium, ISP-culture medium 1; peptone-yeast-Fe-agar culture medium, ISP-culture medium 6; and tyrosine-agar culture medium, ISP-culture medium 7; cultivation at 27° C.) in all cases)

The test results are positive in the case of tryptone-yeast-broth culture medium (ISP-culture medium 1) and peptone-yeast-Fe-agar culture medium (ISP-culture medium 6). In the tyrosine-agar culture medium (ISP-culture medium 7), a very small amount of melanine-like pigments was formed.

(6) Availability of carbon sources (Pridham-Gottlieb agar culture medium, ISP-culture medium 9, cultivation at 27° C.)

The microorganisms grow by utilizing L-arabinose, D-glucose, D-fructose, sucrose, inositol and D-mannitol. Probably, D-xylose may also be utilized. On the other hand, rhamnose, raffinose and lactose are not utilized.

(7) Dissolving of calcium malate (calcium malate-agar culture medium, caltivation at 27° C.)

The test results were negative.

(8) Nitrate-reducing reactions (aqueous peptone solution containing 0.1% potassium nitrate, ISP-culture medium 8, cultivation at 27° C.)

The test results were positive. (9) Decomposition of cellulose (synthetic solution to which filter paper pieces have been added, cultivation at 27° C.)

No growth of the microorganisms has been observed.

In summary, it can be said that the microorganisms of strain MI384-DF12 have aerial hyphae extended and having spiral spore chains and characteristic pseudosporangia. The spore chains each have at least 20 spores, and the spore surface is smooth. In a number of culture media, the microorganisms have a color of light brown to dark brown, although, in certain culture media, the microorganisms have a pink color. There are many cases where no adherence of aerial hyphae is observed, although white aerial hyphae are observed in ISP-culture media 2, 3, 4 and 5. Depending on culture media, the soluble pigments have either a pink shade or a brown shade. The formation of melanine-like pigments are positive, the protein-decomposing action is of a middle strength, and the starch hydrolysis is of a middle degree. The cell walls contain LL-2,6-diaminopimelic acid.

In view of the test data described above, it is considered that the microorganisms of strain MI384-DF12 belong to Streptomyces. From the prior publica-tions, it is revealed that there are the following two kinds of known microorganisms having pseudosporangia, which are regarded as one of the characteristic features of strain MI384-DF12.

*Streptomyces paradocus*

International Journal of Systematic Bactriology, 36, 573-576 (1986); and Systematic and Applied Microbiology, 8 61-64 (1986), and

*Streptomyces vitaminophillus*

International Journal of Systematic Bactriology, 36, 573-576 (1986); Systematic and Applied Microbiology, 8 61-64 (1986), and International Journal of Systematic Bactriology, 33, 557-564 (1983). *Streptomyces vitaminophillus* are distinguished from strain MI384-DF12 in view of vitamin requirements.

In consideration of the above-mentioned matters, the strain MI384-DF12 was identified as "Streptomyces sp. MI384-DF12".

A sample of the strain MI384-DF12 was deposited in the Institute of Applied Microbiology, Tokyo, Japan on Feb. 8, 1990 and given Accession No. 11270. This deposition was converted into the international deposition under the Budapest Treaty on Jan. 18, 1991 and given Accession No. FERM BP-3228.

The nature of the strain MI384-DF12 is easily changeable as in the case of other Streptomyces microorganisms. For instance, there might be naturally or artificially induced mutant microorganisms derived from the strain MI384-DF12 or homologs thereof. It is possible, in the process for the production of benastatins according to the invention, to employ all kinds of microorganisms of Streptomyces, including those subjected to transductions or gene recombinations, as far as such microorganisms are benastatin-producing microorganisms.

According to the present invention, the above-mentioned microorganisms are grown in a culture medium which contains conventional nutrients employed for microorganisms. As carbon sources, use may be made, for instance, glucose, millet-jelly, dextrine, sucrose, starch, molasses, animal and vegetable oils and fats, and the like. Examples of nitrogen-containing nitrients are soybean powder, embryo buds of wheat, corn steep liquor, cotton seed cake, meat extract, peptone, yeast extract, ammonium sulfate, sodium nitrate, urea, etc. As optinal nutrients, it is generally preferred to use inorganic salts which can produce ions of sodium, cobalt, chloride, phosphate, sulfate, etc. It is also possible to use various organic and inorganic substances which can help the growth of microorganisms and which can promote the production of benastatins, which are physiologically active substances.

For the growth of microorganism, it is suitable to carry out a cultivation method, particularly a deep cultivation method, under aerobic conditions. The cultivation is preferably carried out at a temperature of 15° to 37° C., more preferably a temperature of about 26° to 30° C. The production of benastatins, physiologically active substances, may depend on culture media and cultivation conditions. In the case of shake and tank cultivation, it can generally be said that the amount of benastatins accumulated will usually arrive at a maximum value after about 1 to 10 days from the start of cultivation. When the amount of benastatins has reached a maximum value in the culture, then the cultivation is stopped, and the culture medium is subjected to a purification operation to isolate the aimed product.

When a benastatin-containing culture medium obtained according to the invention is purified to obtain the desired product, it is possible to employ a combination of conventional separation procedures in consideration of the nature of the culture medium. Benastatins A and B will be present not only in the filtrate of the culture medium but also in the bodies of microorganisms. The filtrate may be subjected to an extraction treatment with immiscible organic solvents such as ethyl acetate and the like. The microorganism-containing portion may be subjected to an extraction treatment wherein the operation is effected with organic solvents such as methanol, acetone and the like to obtain an extract, which is then concentrated under reduced pressure and thereafter subjected to a further extraction with solvents in a manner similar to that employed in the extraction of the filtrate.

It is also possible to isolate beneastatin A or B as a pure form by any of known methods for the separation of fat-soluble substances, for instance, an adsorption chromatography, a gel filtration chromatography, a thin layer chromatography, a high performance liquid chromatography and the like, or a suitable combination thereof. If necessary, such operations may be carried out repeatedly.

Pharmaceutically acceptable salts of benastatin A or B may be prepared in a conventional manner. For instance, benastatin A or B may be treated with a solution of sodium hydroxide, potassium hydroxide, lithium hydroxide, calcium hydroxide or the like to obtain an appropriate benastatin salt.

In the third aspect of the invention, there is provided a pharmaceutical composition for the inhibition of glutathione transferase, for immunomodification and for the control of microorganism, which comprises benastatin A or B or a pharmaceutically acceptable salt thereof as an active ingredient and a pharmaceutically acceptable carrier.

In the composition according to the invention, it is possible to use any of conventional carriers without any limitations.

The amount of the active ingredient in the composition will vary depending, e.g., on the dosage form of the composition, and may generally be between in the range of about 0.05 and 99%. In a formulation for injection, the amount of the active ingredient may be between in the range of about 0.1 and 50%. A formulation for the administration route other than injection may contain about 1–60% the active ingredient. In the formulations, the remainder components may be conventional carriers.

As shown in the test data given below, benastatins A and B have an activity of significantly inhibiting glutathione transferases, which are enzymes locally present on cell membranes and also in cytoplasms. Furthermore, benastatins have an immunomodifier activity and have an activity as antibiotics. Benastatins have no toxicity. Therefore, benastatins A and B are very useful as glutathione transferase inhibitors, as immunomodifiers and as antibiotics. Benastatin A and B may usually be administered to a warm-blooded animal including a human being in a manner of oral admistration or parenteral administration including intravenous, hypodermatic and intramuscular administrations for the inhibition of glutathione transferases present in the animal body, for immunomodification and for the control of microorganisms.

Thus, in the forth aspect of the invention there is provided a method for the inhibition of glutathione transferases, for immunomodification and for the control of microorganisms, which comprises administering an effective amount of benastatin A or B or a pharmaceutically acceptable salt thereof to a warm-blooded animal.

In particular, benastatin A is excellent in an immunosuppression activity, and benastatin B is excellent in an immunopotentiation activity.

Accordingly, in the fifth aspect of the invention, there is provided a method for immunosuppression, which comprises administering an effective amount of benastatin A or a pharmaceutically acceptable salt thereof to a warm-blooded animal. In the sixth aspect of the invention, there is provided a method for immunopotentiation, which comprises administering an effective amount of benastatin B or a pharmaceutically acceptable salt thereof to a warm-blooded animal.

The dose will vary depending on the state of patients, administration manner, etc. Usually, the dose is 0.05–150 mg/kg/day, preferably 0.5–100 mg/kg/day, more preferably 1–50 mg/kg/day.

The active ingredient according to the invention may be administered in the form of conventional formulations. In the case of oral administration, use may be made of tablets, granules, capsules and the like prepared by using conventional carriers, for instance, known excipients such as dextrine, etc. In the case of parenteral administration, use may be made, for example, of formulations for injections which are usually prepared with adjuvants including physiological saline, solubilizing agents, etc.

As explained in the foregoings, the invention provides benastatins A and B which are novel, physiologically active substances and which have activities of significantly inhibiting glutathione transferases, of immunomodification and of the control of microorganisms. Accordingly, benastatins A and B are very useful for the inhibition of glutathione transferases, for immunomodification and for the control of microorganisms.

The invention will be illustrated in more detail referring to Examples.

EXAMPLE 1

Production of benastatin A

For the initial cultivation, use was made of a culture medium containing 2.0% galactose, 2.0% dextrine, 1.0% Bactosoyton (manufactured by Difco Co., Ltd.), 0.5% cornsteep liqur (manufactured by Iwaki Co., Ltd.), 0.2% ammonium nitrate, 0.2% calcium carbonate, and 0.05% of a mixture of Silicone KM-70 (trade name) as foaming agent (manufactured by Shin-etsu Kagaku Co., Ltd.) and soybean oil (J.P.) (mixing ratio of 1:1). The initial culture medium was adjusted to pH 7 before the sterilization.

110 ml of the initial culture medium was supplied to a 500 ml Erlenmeyer flask, and subjected to sterilization treatment at 120° C. for 20 minutes. The culture medium was inoculated with 1 or 2 platinum loop of *Streptomyces sp.* MI384-DF12 which had been grown by slant cultivation. Shake cultivation was effected at 30° C. for 3 days by employing a rotary vibrator at 180 rpm.

For the next cultivation, use was made of a culture medium containing 2.0% glycerin, 1.5% "Esusanmito" (manufactured by Ajinomoto Co., Ltd.), 0.1% dipotassium hydrogen phosphate, and 0.0005% cobalt chloride hexahydrate. After the culture medium was adjusted to pH 6.2 with 1M monopotassium phosphate, 110 ml of the culture medium was supplied to a 500 ml Erlenmeyer flask, and subjected to sterilization treatment at 120° C. for 20 minutes. 2 ml of the initial cultivation medium was supplied to the culture medium, and the cultivation was effected at 27° C. for 4 days in a manner of shake cultivation. After the cultivation, the resultant cultivation medium was filtered to separate into a cultivation filtrate and a microorganism-containing portion.

9.8 l of the above-mentioned cultivation filtrate was admixed with 10 l of ethyl acetate, and then sufficiently stirred to extract the desired component therefrom. The resulting extract was concentrated to obtain 3.52 g of a crude product having a red color. The crude product was dissolved in 20 ml of methanol, admixed with 20 g of a silanized silica gel ("Art. 7719", manufactured by Merck Company), and then concentrated to dryness. The dry product was suspended in 40% methanol, and the resultant suspension was subjected to a column chromatography wherein use was made of a 400 ml column filled with a silanized silica gel and 40% methanol and the desired component was separated by employing a linear gradient of 40–100% methanol. The desired component-containing fractions were concentrated to dryness to obtain 878.7 mg of a red product, which was then dissolved in 10 ml of methanol. The methanol solution was admixed with 10 g of a silica gel ("YMC-GEL ODS-A60-200/60, manufactured by Yamamura Kagaku Kenkyusho Co., Ltd.), and concentrated to dryness. The resultant product was suspended in 40% methanol, and then subjected to a column chromatography wherein use was made a 200 ml column filled with "YMC-GEL" and 40% methanol and the desired component were separated by employing a linear gradient of 40–100% methanol. The product thus obtained was concentrated to dryness to give 329.2 mg of a brown powder, which was then dissolved in 10 ml of methanol, thereafter admixed with 10 g of silica gel 60 ("Art. 7734", manufactured by Merck Company) and concentrated to dryness The dry product thus obtained was suspended in a mixture of chloroform and methanol (90:10), and the resultant suspension was subjected to a column chromatography wherein use was made of a 200 ml column filled with silica gel 60 and the same solvent mixture, and washed with the same solvent mixture. Then, the desired component was separated by employing a mixture of chloroform and methanol (85:15) as eluant, and concentrated to dryness, thus 115.1 mg of highly purified benastatin A was obtained as yellow powder. The UV absorption spectral data, the IR absortion spectral data, the $^1$H-NMR spectral data and the $^{13}$C-NMR spectral data of the purified benastatin A are shown in FIGS. 1, 2, 3 and 4, respectively.

In the cultivation steps and the purification steps, the detection of benastatin A was effected by the measurement of glutathione transferase inhibition activity. This measurement was performed according to a method similar to that for the measurement of glutathione transferase inhibition activity shown in Pharmacological Test 1 given below.

EXAMPLE 2

Production of benastatin B

Shake cultivation operation was carried out as in the case of Example 1. After the cultivation, the resultant cultivation medium was filtered to separate into a cultivation filtrate and a microorganism-containing portion. 30 l of the cultivation filtrate was admixed with 30 l of ethyl acetate, and sufficiently stirred to extract the desired component, which was then concentrated to give 12.32 g of a crude product having a red color.

The crude red product thus obtained was dissolved in 40 ml of methanol, then admixed with 40 g of a silanized silica gel ("Art. 7719", manufactured by Merck Company), and concentrated to dryness under reduced pressure. The resultant dry product was suspended in 40% methanol, and the suspension thus prepared was subjected to a column chromatography wherein use was made of a 500 ml column filled with a silanized silica gel and 40% methanol, and the desired component was separated by employing a linear gradient of 40 to 100% methanol, and concentrated to dryness to obtain 6.36 g of a product having a red color.

The red product thus obtained was dissolved in 20 ml of methanol, admixed with 20 g of silica gel ("YMC-GEL ODS-A60-200/60, manufactured by Yamamura Kagaku Kenkyusho Co., Ltd.), and then concentrated to dryness. The resulting dry product was suspended in 40% methanol, and subjected to a column chromatography wherein use was made of a 500 ml column filled with "YMC-GEL" and 40% methanol. The desired component was separated by employing a linear gradient of 40 to 100% methanol, and concentrated to dryness to obtain 3.29 g of a brown powder product.

The brown product was dissolved in 20 ml of methanol, admixed with 20 g of silica gel 60 ("Art. 7734", manufactured by Merck Company), and then concentrated to dryness. The resultant dry product was suspended in chloroform, subjected to a column chromatography wherein use was made of a 400 ml column filled with silica gel 60 and chloroform, and washed with the same solvent. The desired component was separated with a mixture of chloroform and methanol (95:5), and then concentrated to dryness to obtain 1.35 g of a yellow powder product.

The yellow powder product was subjected to a high performance liquid chromatography wherein use was made of an HPLC column (Capcell Pak $C_{18}$, 20ϕ×250 mm, manufactured by Shiseido Co., Ltd.; flow rate 8 ml/min.) previously equilibrated with 78% acetonitrile containing 1% acetic acid. The elution was effected by the use of the equilibration liquid as mentioned above to obtain an active fraction, which was then concentrated to dryness to give 92.7 mg of highly purified benastatin B as yellow powder. The UV absorption spectral data, the IR absorption spectral data, the $^1$H-NMR spectral data and the $^{13}$C-NMR spectral data of the pure benastatin B are shown in FIGS. 5, 6, 7 and 8, respectively.

The detection of benastatin B in the cultivation and purification steps was effected as in the case of Example 1.

EXAMPLE 3

Production of benastatin tablets 30 parts by weight of benastatin A or B, 120 parts by weight of crystalline lactose, 147 parts by weight of crystalline cellulose and 3 parts by weight of magnesium stearate were mixed with each other in V-shape mixer, and the resulting mixture was formulated into tablets, each of which had 300 mg of benastatin A or B.

Next, pharmacological test data are given below, in order to demonstrate that benastatins A and B have an activity for inhibiting glutathione transferases, for immunomodification and for combatting microorganisms, and have no toxicity.

Pharmacological Test 1

Glutathione transferase inhibition activity of benastatins A and B

The glutathione transferase inhibition activity was determined by a modified method based on the known method described in Biochemical and Biophysical Research Communications, 112, 980–985 (1983).

A test tube was charged with a solution mixture consisting of (a) 0.1 ml of 90 mM glutathione (reduction type), (b) 0.05 ml of 20 mM 3,4-dichloronitrobenzene, (c) 1.7 ml of 0.1M potassium phosphate buffer solution (pH 7.4) and (d) 0.1 ml of an aqueous solution containing the test compound. The solution mixture was heated to 37° C. for 3 minutes, and admixed with 0.05 ml of a glutathione transferase solution to effect a reaction at 37° C. for 30 minutes. The glutathione transferase solution employed was one which had been obtained from a homogenate of rat liver and which had been patially refined by means of a DEAE-cellulose column and of salting out-operation with ammonium sulfate.

After the completion of the reaction, the sample was measured for the light absorption (a) at 345 nm. At the same time, a control sample which was free of the test compound and which contained only the buffer solution was measured for the light absorption (b) at 345 nm.

The glutathione transferase inhibition activity was determined according to the formula:

$$[(b-a)/b] \times 100$$

$IC_{50}$, which is the concentration of a test compound required for 50% inhibition, was recorded. According to this determination method, it has been found that $IC_{50}$ of purified benastatin A is 2.50 μg/ml, while $IC_{50}$ of benastatin B is 0.92 μg/ml.

Pharmacological Test 2

Immunosuppression activity of benastatin A

A pharmacological test was made about a suppression activity of benastatins on the lymphocyte blast formation reaction.

In this test, use was made of an RPMI 1640 culture medium supplemented with 20% bovin fetus serum, 25 mM Hepes buffer, 100 μg/ml streptomycin and 100 units/ml penicillin G. The cultivation was effected by using microplate (COSTAR) with a flat bottom and with 96 wells. As mitogens, use was made of lipopolysaccharide (LPS) and concanavalin A (Con A) at concentrations of 100 and 5 μg/ml, respectively.

After spleen cells were taken out from BALB/c mouse (female, 25 weeks old), a unicellular suspension of the spleen cells was prepared, and then subjected to a hyper shock treatment to remove erythrocytes therefrom.

Each well was charged with 0.2 ml of a sample which contained $2 \times 10^5$ spleen cells and the test compound at a predetermined concentration. The cultivation was conducted for 72 hours. Before 8 hours from the completion of cultivation, each well was further charged with 37 KBq of [$^3$H]-thymidine to determine the amount of the thymidine taken into the cells.

The effect of the test compound was estimated by comparing the test compound-containing sample with the control sample with respect to the amount of [$^3$H]-thymidine taken into the cells [Men-eki Jikken Sousa-ho (Guidebook of Immunological Experiments), edited by the Japanese Immunological Society, pp. 267–2276].

In both the LPS-added samples and the Con A-added samples, it was observed that benastatin A exerted a suppression activity on lymphocyte blast formation reaction, while the intensity of the activity varied depending on the concentration of benestatins. The activity was recorded as $IC_{50}$, which is the concentration of benastatins required for 50% suppression, i.e., 50% decrease in the amount of [$^3$H]-thymidine taken into the cells. $IC_{50}$ of benastatin A in the case of LPS was 7.7 μg/ml, and $IC_{50}$ in the case of Con A was 7.3 μg/ml.

Pharmacological Test 3

Activity of benastatins A and B as antibiotics

The minimum of microorganism growth inhibition concentrations of benastatins A and B were determined for various bacteria, east and fungi according to a conventional agar dilution assay method. The results are shown in Table 1. It will be seen from Table 1 that benastatins A and B have a satisfactory antimicrobial activity, particularly against gram-positive bacteria, etc.

TABLE 1

| Microorganism | Minimum growth inhibition concentration (μg/ml) | |
|---|---|---|
| | Benastatin A | Benastatin B |
| Staphylococcus aureus Smith | 3.12 | 3.12 |
| Staphylococcus aureus MS9610 | 3.12 | 3.12 |
| Staphylococcus aureus No. 5 (MRSA)* | 3.12 | 3.12 |
| Staphylococcus aureus No. 17 (MRSA)* | 3.12 | 3.12 |
| Micrococcus luteus FDA16 | 3.12 | 3.12 |
| Bacillus subtilis NRRL B-558 | 3.12 | 3.12 |
| Bacillus cereus ATCC10702 | 3.12 | 3.12 |
| Corynebacterium bovis 1810 | 3.12 | 3.12 |
| Escherichia coli NIHJ | 100 | 100 |
| Shigella dysenteriae JS11910 | >50 | >50 |
| Salmonella typhi T-63 | >50 | >50 |
| Proteus rettgeri GN311 | 50 | 50 |
| Pseudomanas aeruginosa A3 | >50 | 50 |
| Klebsiella pneumoniae PCI602 | >50 | >50 |
| Mycabacterium smegmatis ATCC607 | 50 | 12.5 |
| Candida tropicalis F-1 | >50 | >50 |
| Saccharomyces cerevisiae F-7 | >100 | >50 |
| Cryptococcus neoformans F-10 | 50 | 50 |
| Cochliobolus miyabeanus | >25 | >25 |
| Pyricularia oryzae | 50 | 50 |
| Aspergillus niger F-16 | >50 | >100 |

*MRSA: Methicillin resistant Staphylococcus aureus

Pharmacological Test 4

Immunomodifier activity of benastatin B (1) Test compound

In lymphocyte blast formation reaction, use was made of benastatin B as a solution prepared in a manner, wherein benastatin B was dissolved in methanol and admixed with PBS(-), with the proviso that the concentration of methanol in the final solution was 0.5%.

In the graft versus host reaction (GvH), use was made of benastatin B dissolved in physiological saline.

(2) Methods (a) Effect on lymphocyte blast formation reaction

For the cultivation, use was made of RPMI 1640 culture medium supplemented with 20% bovine fetus serum, 25 mM Hepes buffer, 100 μg/ml streptomycin and 100 units/ml penicillin G. The cultivation was carried out in a microplate (COSTAR) with flat bottom and with 96 wells. As the mitogens, lipopolysaccharide (LPS) and concanavalin A (Con A) were used at the final concentrations of 100 μg/ml and 5 μg/ml, respectively.

Spleen cells were taken out from BALB/c mouse (female, at most 20 weeks old) to prepare a unicellular dispersion of spleen cells. This dispersion was subjected to a hyper shock treatment to remove erythrocytes therefrom. The resulting spleen cell sample was directly used in the test employing LPS. Alternatively, the spleen cell sample was filtered through Nylon Fiber (manufactured by Wako Jun-yaku Co., Ltd.) for removing T cells therefrom, and then the cell sample was used in the test employing Con A.

Each well was charged with 0.2 ml of a test sample containing $2 \times 10^5$ murine spleen cells and the test compound at a predetermined concentration. The cultivation was effected for 72 hours. Before 8 hours from the termination of the cultivation, the wells each were charged with 37 KBq of [$^3$H]-thymidine in order to determine the amount of thymidine taken into the cells. The effect of the test compound was estimated by comparing the test samples with the control samples, with respect to the amount of [$^3$H]-thymidine taken into the cells.

(b) Effect on graft versus host reaction (GvH)

The effect on GvH was estimated according to a modified method based on the method described in M.

Simonsen et al, "A study of the graft versus host reaction in transplantation to embryos, F1 hybrids, and irradiated animals", Ann. N.Y. Acad. Sci., 73, 834-841 (1978).

Spleen cells were taken out from C57BL/6 mouse (female, 10 weeks old) to prepare a murine spleen cell sample containing $5 \times 10^6$ spleen cells according to the method as mentioned above. The spleen cell sample was transplanted into the abdominal cavity of BDF1 mouse (7 days old) as the F1 acceptor. The test compound at a predetermined concentration was subcutaneously injected over a period of time of 3 days including the initial day of said transplantation. After 7 days from the inital transplantation, measurements were made about the body weight and the spleen weight of the $BDF_1$ mouse to calculate the ratio (mg/g) of spleen weight (mg) to body weight (g).

(3) Results

Table 2 shows the test data relating to the effect of benastatin B on lymphocyte blast formation reaction. It will be seen from Table 2 that benastatin B, when used at a low concentration, potentiates lymphocyte blast formation reaction induced by LPS, although the benastatin B, when used at a higher concentration of at least 12.5 µg/ml, significantly suppresses this reaction.

In the case of lymphocyte blast formation reaction induced by Con A, it has been observed that benastatin B, when used at a concentration of at least 6.25 µg/ml, significantly suppresses this reaction.

Table 3 shows the test data concerning the effect of benastatin B on GvH. It has been observed that benastatin B, when used in various amounts, significantly promotes GvH, while the benastatin B, when used in a lower amount, strongly potentiates this reaction.

TABLE 2

Effect of benastatin B on LPS- or Con A-induced murine lymphocyte blastogenesis in vitro

| Sample | Concentration (µg/ml) | Stimulation index (%) LPS | Con A |
|---|---|---|---|
| Control | — | 100 | 100 |
| Benastatin B | 3.13 | 147.5* | 106.2* |
| | 6.25 | 138.0* | 12.6 |
| | 12.5 | 58.9 | 26.8 |
| | 25 | 0.2* | 1.0* |
| | 50 | 0.4* | 1.0 |
| | 100 | 0.2* | 0.9* |

*$p < 0.05$ vs control.

TABLE 3

Effect of benastatin B on GvH in vivo

| Sample | Dose (mg/kg) | Number of mice | Spleen/body weight (mg/kg) | Index |
|---|---|---|---|---|
| Non induced | | 10 | 4.5 ± 0.3 | 1.00 |
| Induced | | 9 | 8.3 ± 2.5 | 1.84 |
| Benastatin B | 0.5 | 10 | 12.5 ± 2.2 | 2.78* |
| | 5 | 11 | 11.5 ± 0.8 | 2.56* |
| | 50 | 11 | 10.6 ± 1.3 | 2.36* |

*$p < 0.05$ vs control.

PHARMACOLOGICAL TEST 4

Toxicity of Benastatins A and B

Benastatins A and B were each administered to the abdominal cavity of a mouse to examine the toxicity thereof. No toxicity was observed even when benastatins A and B were each administered in a large amount of 100 mg/kg.

What we claim is:

1. Benastatins A and B, which are physiologically active substances having the formula (I):

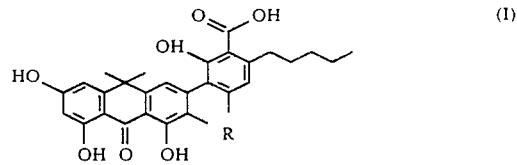

wherein R represents —$CH_2$—$CH_2$— or —CH=CH—, or pharmaceutically acceptable salts thereof.

2. A phamaceutical composition for the glutathione transferase inhibition, for immnomodification or for the control of microorganism, which comprises benastatin A or B or a pharmaceutically acceptable salt thereof and a pharmaceutically acceptable carrier.

3. A method for the inhibition of glutathione trasferases, for immunomodification or for the control of microorganism, which comprises administering an effective amount of benastatin A or B or a pharmaceutically acceptable salt thereof to a warm-blooded animal.

* * * * *